United States Patent
Youker et al.

(10) Patent No.: US 7,813,801 B2
(45) Date of Patent: Oct. 12, 2010

(54) IMPLANTABLE MEDICAL DEVICE POWERED BY RECHARGEABLE BATTERY

(75) Inventors: Nick A. Youker, River Falls, WI (US); Robert S. Harguth, Ham Lake, MN (US); Keith R. Maile, New Brighton, MN (US); Michael J. Root, Lino Lakes, MN (US); Cheng Zhang, Vadnais Heights, MN (US); Abhi Chavan, Maple Grove, MN (US); Paul Huelskamp, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 816 days.

(21) Appl. No.: 11/610,894

(22) Filed: Dec. 14, 2006

(65) Prior Publication Data
US 2007/0150019 A1    Jun. 28, 2007

Related U.S. Application Data

(60) Provisional application No. 60/750,565, filed on Dec. 15, 2005.

(51) Int. Cl.
*A61N 1/00* (2006.01)
(52) U.S. Cl. ........................................... 607/29
(58) Field of Classification Search ................. 606/169; 607/29; 600/515, 300; 128/848; 623/2.37; 429/91; 320/107, 136
See application file for complete search history.

(56) References Cited

U.S. PATENT DOCUMENTS

| | | | |
|---|---|---|---|
| 5,411,537 A | 5/1995 | Munshi et al. | |
| 5,432,429 A * | 7/1995 | Armstrong et al. | 320/136 |
| 5,702,431 A | 12/1997 | Wang et al. | |
| 5,713,939 A | 2/1998 | Nedungadi et al. | |
| 5,747,189 A * | 5/1998 | Perkins | 429/91 |
| 5,749,909 A | 5/1998 | Schroeppel et al. | |
| 6,114,838 A | 9/2000 | Brink et al. | |
| 6,167,309 A | 12/2000 | Lyden | |
| 6,238,813 B1 | 5/2001 | Maile et al. | |
| 6,277,078 B1 | 8/2001 | Porat et al. | |
| 6,490,484 B2 | 12/2002 | Dooley et al. | |
| 6,552,511 B1 | 4/2003 | Gayram | |
| 6,584,355 B2 | 6/2003 | Stessman | |
| 6,586,850 B1 | 7/2003 | Powers | |
| 6,631,293 B2 | 10/2003 | Lyden | |
| 6,639,381 B2 | 10/2003 | Tamura et al. | |
| 6,764,446 B2 | 7/2004 | Wolinsky et al. | |
| 6,909,915 B2 | 6/2005 | Greatbatch et al. | |
| 6,937,894 B1 * | 8/2005 | Isaac et al. | 607/5 |
| 7,194,308 B2 | 3/2007 | Krig et al. | |
| 2004/0158296 A1 | 8/2004 | Greatbatch et al. | |
| 2004/0215092 A1* | 10/2004 | Fischell et al. | 600/515 |
| 2004/0236192 A1 | 11/2004 | Necola Shehada et al. | |
| 2005/0037256 A1 | 2/2005 | Mukainakano | |
| 2005/0088140 A1* | 4/2005 | Bushong et al. | 320/107 |
| 2006/0009818 A1 | 1/2006 | Von Arx et al. | |
| 2006/0077762 A1* | 4/2006 | Boland et al. | 367/170 |

\* cited by examiner

*Primary Examiner*—Goerge Manuel
*Assistant Examiner*—Robert N Wieland
(74) *Attorney, Agent, or Firm*—Schwegman, Lundberg & Woessner, P.A.

(57) ABSTRACT

A battery management circuit provides an implantable medical device with power management that allows safe and efficient use of a rechargeable battery. Various ways of monitoring the energy level of the rechargeable battery and controlling the battery recharging process for user convenience and safety are provided.

44 Claims, 14 Drawing Sheets

IMPLANTABLE MEDICAL DEVICE POWERED BY RECHARGEABLE BATTERY

CROSS-REFERENCE TO RELATED APPLICATION(S)

This application claims the benefit of U.S. Provisional Application No. 60/750,565, filed on Dec. 15, 2005, under 35 U.S.C. §119(e), which is hereby incorporated by reference.

TECHNICAL FIELD

This document relates generally to implantable medical devices and particularly, but not by way of limitation, to methods and systems for powering implantable medical device using rechargeable battery.

BACKGROUND

Medical devices are implanted in human bodies for monitoring physiological conditions, diagnosing diseases, treating diseases, or restoring functions of organs or tissues. Examples of such implantable medical devices include cardiac rhythm management (CRM) devices, neural stimulators, neuromuscular stimulators, drug delivery devices, and biological therapy devices. One particular example of implantable medical devices is a CRM device implanted in a patient to treat irregular or other abnormal cardiac rhythms by delivering electrical pulses to the patient's heart. Such rhythms result in diminished blood circulation. Implantable CRM devices include, among other things, pacemakers, also referred to as pacers. Pacemakers are often used to treat patients with bradyarrhythmias, that is, hearts that beat too slowly or irregularly. Such pacemakers may coordinate atrial and ventricular contractions to improve the heart's pumping efficiency. Implantable cardiac management devices also include defibrillators that are capable of delivering higher energy electrical stimuli to the heart. Such defibrillators may also include cardioverters, which synchronize the delivery of such stimuli to portions of sensed intrinsic heart activity signals. Defibrillators are often used to treat patients with tachyarrhythmias, that is, hearts that beat too quickly. In addition to pacemakers and defibrillators, implantable CRM systems also include, among other things, pacer/defibrillators that combine the functions of pacemakers and defibrillators, drug delivery devices, and any other implantable systems or devices for diagnosing or treating cardiac arrhythmias.

Batteries are used as energy sources for implantable medical devices. While the use of battery allows a medical device to be totally implantable, without the need of transcutaneous power transmission, the power consumption and the longevity of the medical device is limited by the capacity of the battery. For example, most treatment using implantable CRM devices are long-term treatments that may last up to the patient's lifetime. When the battery of an implantable CRM device is no longer able to provide sufficient energy for the operation of the device, the device is to be explanted and replaced with a new device. In other words, the longevity of the implantable CRM device depends on the longevity of its battery. Additionally, the feasibility of introducing a new feature to an implantable medical device depends on the impact on its power consumption. One way to extend the longevity of an implantable medical device and/or to allow incorporation of a new feature into the implantable medical device is to use rechargeable battery. However, issues unique to a rechargeable battery exist. For example, repeated recharging processes may create significant inconvenience to the patient. The power supply to the implantable medical device may be interrupted during each recharging process, causing substantial risk when the device is life-supporting, such as in the case of some implantable CRM devices.

For these and other reasons, there is a need to provide an implantable medical device with a battery management system that allows safe and efficient use of a rechargeable battery.

SUMMARY

A battery management circuit provides an implantable medical device with power management that allows safe and efficient use of a rechargeable battery. Various ways of monitoring the energy level of the rechargeable battery and controlling the battery recharging process for user convenience and safety are provided.

In one embodiment, an implantable medical device includes a power source including a rechargeable battery, a battery status monitor, a recharging controller, and a recharging circuit. The battery status monitor monitors a parameter indicative of state of charge of the rechargeable battery. The recharging controller controls a process of recharging the rechargeable battery using the parameter. The process includes a fast-charge phase and a trickle-charge phase. The recharging circuit includes a power receiver and a power converter. The power receiver receives a power-transmission signal. The power converter converts the power-transmission signal to a constant-current signal during the fast-charge phase and to a constant-voltage signal during the trickle-charge phase.

In another embodiment, an implantable medical device includes a power source including a rechargeable battery, a recharging circuit, and a recharging controller. The recharging circuit recharges the rechargeable battery. The recharging controller includes a primary period timer that initiates a primary period in response to an initiation signal and a secondary period timer that initiates a secondary period when the primary period expires. The recharging controller suspends the recharging of the rechargeable battery during the primary period and controls the recharging of the rechargeable battery during the secondary period.

In another embodiment, an implantable medical device includes a feature circuit and a power source. The feature circuit including one or more of a sensing circuit that senses one or more physiological signals and an electrical stimulation circuit that delivers electrical stimulation. The power source provides power to the feature circuit and includes a rechargeable battery, a non-rechargeable battery, a battery status monitor, and a battery switch. The battery status monitor detects at least one of an energy level of the rechargeable battery and an energy level of the non-rechargeable battery. The battery switch selectively provides electrical connection between the feature circuit and one of the rechargeable battery and the non-rechargeable battery using at least one of the energy level of the rechargeable battery and the energy level of the non-rechargeable battery.

In another embodiment, an implantable sensor module includes a pressure sensor and a power source. The pressure sensor senses a signal indicative of a blood pressure. The power source provides power to the pressure sensor and includes a rechargeable battery, a battery status monitor, a recharging controller, and a recharging circuit. The battery status monitor detects an energy level of the rechargeable battery. The recharging controller controls a process of recharging the rechargeable battery using the energy level. The recharging circuit includes an ultrasonic power receiver and a piezoelectric transducer. The ultrasonic power receiver receives an ultrasonic signal carrying an ultrasonic energy. The piezoelectric transducer converts the ultrasonic energy to an electrical energy for recharging the rechargeable battery.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses the power source of an implantable medical device that includes a rechargeable battery. In addition to the rechargeable battery, the power source includes circuitry for monitoring battery status, recharging the rechargeable battery, and controlling the process of recharging. In one embodiment, the power source includes a non-rechargeable battery in addition to the rechargeable battery. Various embodiments of the power source and its various components are discussed below. These embodiments may be combined with each other and with other embodiments as those skilled in the art will understand by reading this document.

In this document, "a battery", as in "non-rechargeable battery" and "rechargeable battery", includes a single cell or a group of cells connected together to provide electrical energy.

Figure 1:
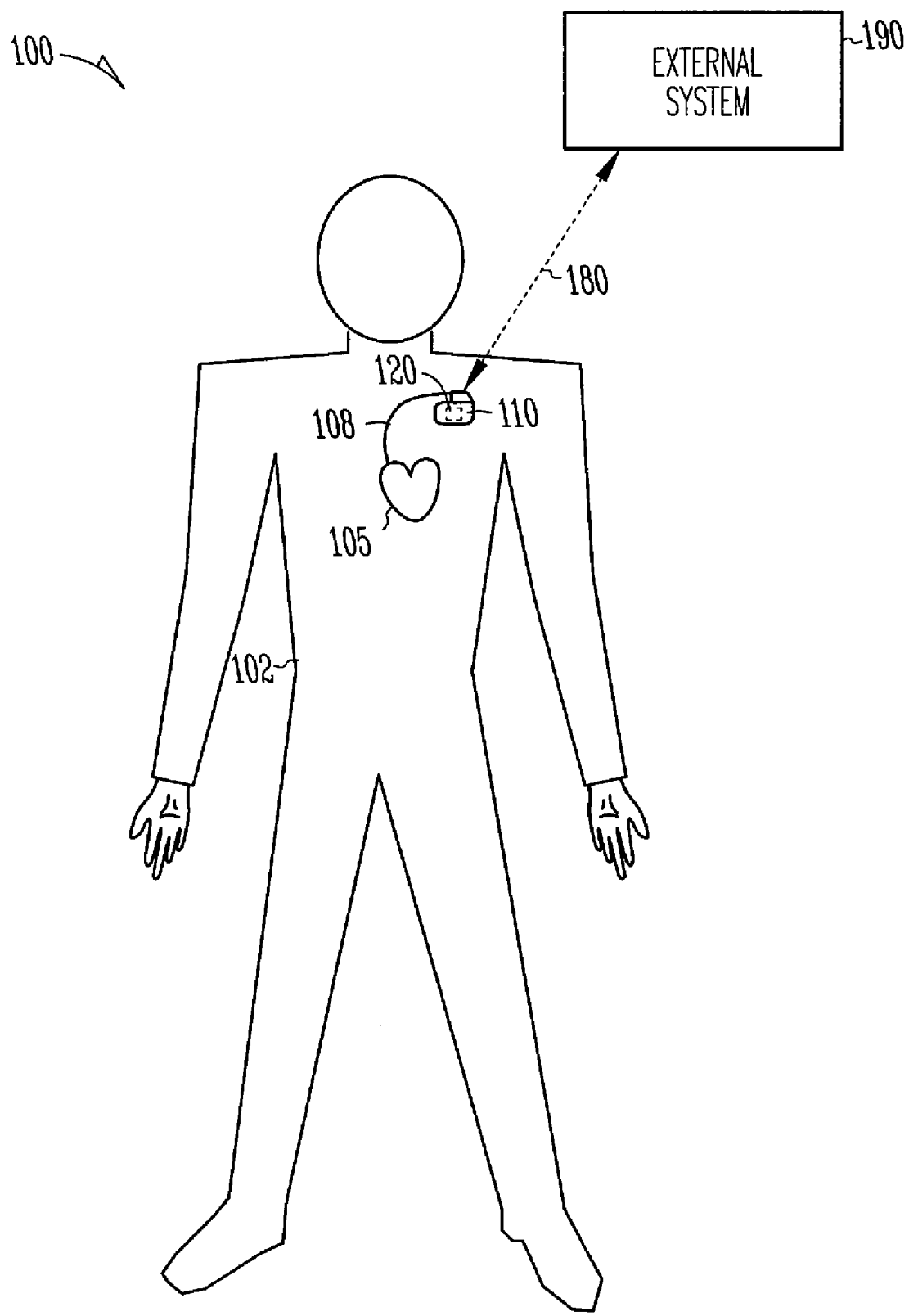
FIG. 1 is an illustration of an embodiment of a system including an implantable medical device and an external system and portions of an environment in which the system is used.

FIG. 1 is an illustration of an embodiment of a system 100 and portions of an environment in which system 100 is used. System 100 includes an implantable medical device 110, a lead system 108, and an external system 190. A wireless telemetry link 180 provides for communication between implantable medical device 110 and external system 190. Implantable medical device 110 includes a power source 120 that includes at least a rechargeable battery and a battery management circuit. While system 100 is a CRM system as shown in FIG. 1 as a specific example, the present subject matter applies to any system that includes one or more battery-powered implantable medical devices.

After implantation, implantable medical device 110 operates within a body 102 of a patient to sense activities of a heart 105 and deliver one or more therapies to heart 105 through lead system 108. In one embodiment, as illustrated in FIG. 1, implantable medical device 110 is an implantable CRM device that delivers one or more therapies including, but are not limited to, a pacing therapy, a cardioversion/defibrillation therapy, a cardiac resynchronization therapy (CRT), a remodeling control therapy (RCT), a drug therapy, and a biological therapy such as a cell therapy and a gene therapy.

Lead system 108 provides one or more electrical connections between implantable medical device 110 and heart 105. In one embodiment, lead system 108 includes one ore more leads each including one or more electrodes configured for endocardial and/or epicardial placement. Pacing and/or cardioversion/defibrillation are delivered to heart 105 through such leads and electrodes. In one embodiment, one or more leads of lead system 108 also include agent delivery ports configured for endocardial, epicardial, and/or intravascular placement. Substances such as chemical or biological agents are delivered to heart 105 through such leads and agent delivery ports.

External system 190 communicates with implantable medical device 110 via telemetry link 180. External system 190 allows for data communication with implantable medical device 110 and power transmission to the implantable medical device. The power transmission provides for recharging of the rechargeable battery when needed. In one embodiment, external system 190 includes an external programmer. In another embodiment, external system 190 includes a portable device, such as a hand-held device, provided for use by the patient or another person providing care to the patient. In another embodiment, external system 190 includes a patient management system including an external device communicating with implantable medical device 110 via telemetry link 180, a network coupled to the external device, and a remote device coupled to the network. Such a patient management system allows a physician or other caregiver to communicate with implantable medical device 110 through the remote device in a distant location.

Telemetry link 180 provides for data transmission between implantable medical device 110 and external system 190 and power transmission from external system 190 to implantable medical device 110. In one embodiment, telemetry link 180 includes a single medium for data transmission and power transmission. For example, a single inductive or ultrasonic couple is used for both data transmission and power transmission. In another embodiment, telemetry link 180 includes a medium for data transmission and another medium for power transmission. For example, a far-field radio-frequency telemetry link is used for data transmission, while an inductive or ultrasonic couple is used for power transmission. Telemetry link 180 also provides for data transmission from implantable medical devices 110 to external system 190. This includes, for example, transmitting real-time physiological data acquired by implantable medical devices 110, extracting physiological data acquired by and stored in implantable medical devices 110, extracting therapy history data stored in implantable medical devices 110, and extracting data indicating an operational status of implantable medical devices, such as battery status and lead impedance. Telemetry link 180 also provides for data transmission from external system 190 to implantable medical devices 110. This includes, for example, programming implantable medical devices 110 to acquire physiological data, programming implantable medical devices 110 to perform at least one self-diagnostic test (such as for a battery status and lead impedance status), programming implantable medical devices 110 to perform a diagnostic task, and programming implantable medical devices 110 to deliver a therapy.

Figure 2:
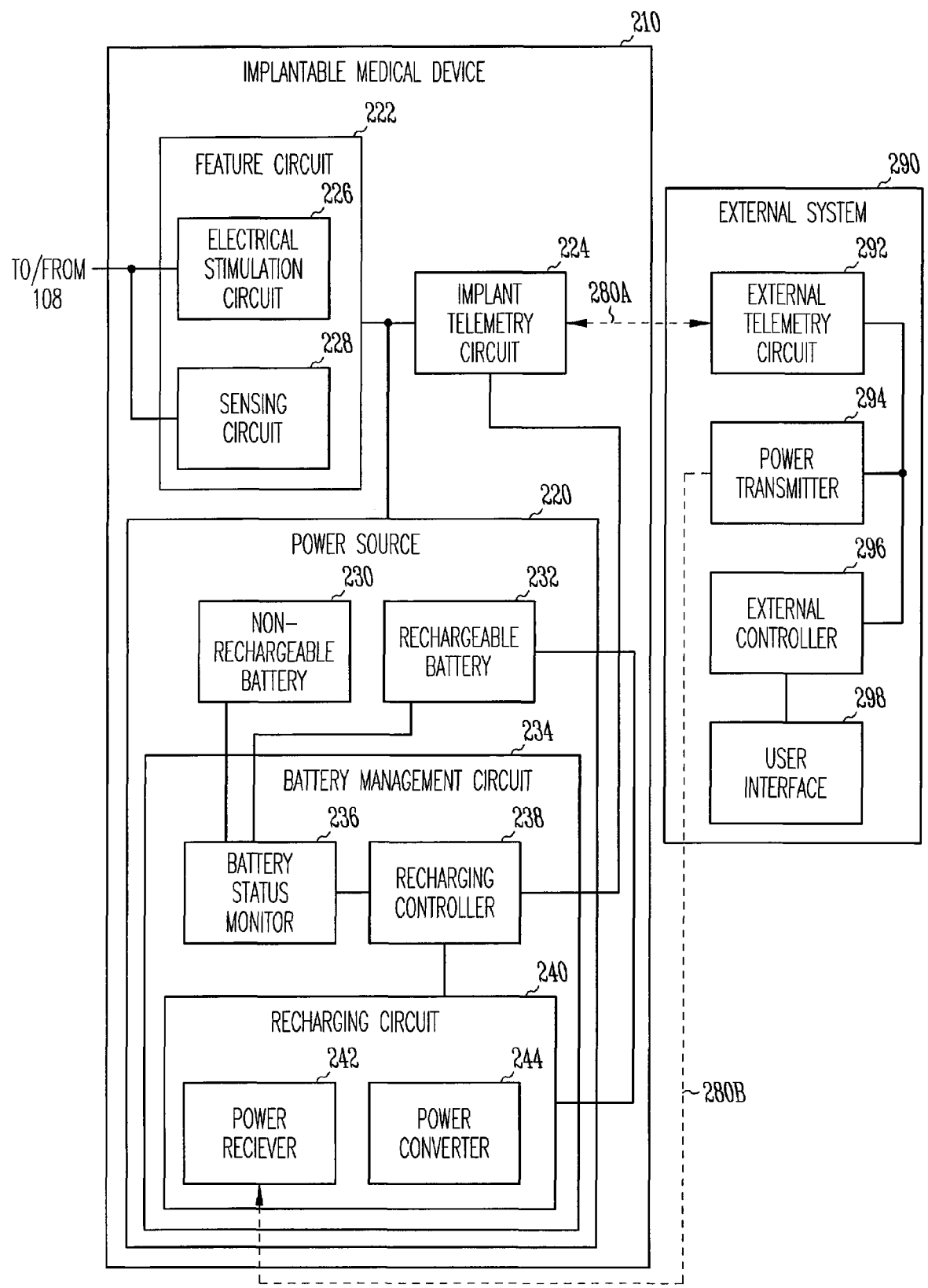
FIG. 2 is a block diagram illustrating an embodiment of circuits of the implantable medical device and the external system.

FIG. 2 is a block diagram illustrating an embodiment of circuits of an implantable medical device 210 and an external system 290. Implantable medical device 210 is a specific embodiment of implantable medical device 110 and includes a feature circuit 222, an implant telemetry circuit 224, and a power source 220. External system 290 is a specific embodiment of external system 190 and includes an external telemetry circuit 292, a power transmitter 294, an external controller 296, and a user interface 298. A data-transmission link 280A provides for data transmission between implantable medical device 210 and external system 290. A power-transmission link 280B provides for power transmission from external device 290 to implantable medical device 210. In one embodiment, data-transmission link 280A and power-transmission link 280B are integrated and use a single medium. In other words, data-transmission link 280A and power-transmission link 280B are each a component of an integrated data-and-power-transmission link. In other embodiments, data-transmission link 280A and power-transmission link 280B are separate and use a plurality of media.

Feature circuit 222 performs one or more of sensing, diagnostic, and therapeutic functions. In one embodiment, as illustrated in FIG. 2, feature circuit 222 includes an electrical stimulation circuit 226 and a sensing circuit 228. Electrical stimulation circuit 226 delivers electrical stimulation to body 102. Examples of electrical stimulation circuit 226 include a pacing circuit that delivers pacing pulses, a cardioversion/defibrillation circuit that delivers cardioversion/defibrillation pulses, and a neural stimulation circuit that delivers neural stimulation pulses. Sensing circuit 228 senses one or more physiological signals such as electrograms, heart sounds or signals indicative of heart sounds, activity level signals, pressure signals, impedance signals, and respiratory signals. In various embodiments, feature circuit 222 includes one or more of electrical stimulation circuit 226, sensing circuit 228, a diagnostic circuit to perform one or more diagnostic functions using the one or more physiological signals sensed by sensing circuit 228, a drug delivery device to deliver one or more pharmaceutical agents, and a biological therapy device to deliver one or more biologic therapies.

Implant telemetry circuit 224 receives signals from external system 290 and transmits signals to external system 290 via data-transmission link 280A. In one embodiment, implant telemetry circuit 224 also allows for communication between implantable medial device 210 and one or more other implantable medical devices implanted within the same patient.

Power source 220 is a specific embodiment of power source 120 and provides feature circuit 222 and implant telemetry circuit 224 with energy required for their operations. In one embodiment, as illustrated in FIG. 2, power source 220 includes a non-rechargeable battery (also known as primary battery) 230, a rechargeable battery (also known as secondary battery) 232, and a battery management circuit 234. Examples of non-rechargeable battery 230 include lithium manganese dioxide and lithium carbon monofluoride batteries. Examples of rechargeable battery 232 include rechargeable lithium and lithium ion batteries. In other embodiments, power source 220 does not include non-rechargeable battery 230. In one embodiment, rechargeable battery 232 is charged to its full capacity at factory. In one embodiment, rechargeable battery 232 is recharged (topped off) to its full capacity during implantation of implantable medical device 210, to compensate for the discharge that has occurred. Battery management circuit 234 includes a battery status monitor 236, a recharging controller 238, and a recharging circuit 240. Battery status monitor 236 monitors the energy level of rechargeable battery 232. In one embodiment, in which power source includes non-rechargeable battery 230, battery status monitor 236 monitors the energy level of each of rechargeable battery 232 and non-rechargeable battery 230. In one embodiment, battery status monitor 236 measures a parameter indicative of a state of charge to represent the energy level. In one embodiment, when the energy level drops below a predetermined threshold, battery status monitor 236 produces an alarm signal or warning message indicative of a low energy level. The alarm signal or warning message is transmitted to external system 290 via data-transmission link 280A. Recharging controller 238 controls the process of recharging rechargeable battery 232. In one embodiment, recharging controller 238 initiates each process of recharging rechargeable battery 232 in response to a user command transmitted from external system 290 via data-transmission link 280A and/or receipt of energy transmitted from external system 290 via power-transmission link 280B.

In one embodiment, after the process of recharging is initiated, recharging controller 238 controls the recharging of rechargeable battery 232 using the energy level of rechargeable battery 232. Recharging circuit 240 is connected to the terminals of rechargeable battery 232 to recharge rechargeable battery 232. Recharging circuit 240 includes a power receiver 242 and a power converter 244. Power receiver 242 receives a power-transmission signal transmitted from external system 290 via power-transmission link 280B. Power converter 244 converts the power-transmission signal to an electrical signal suitable for recharging rechargeable battery 232.

External telemetry circuit 292 transmits signals to implantable medial device 210, and receives signals transmitted from implantable medical device 210, via data-transmission link 280A. Power transmitter 294 transmits the power-transmission signal to implantable medical device 210 via power-transmission link 280B. External controller 296 controls the overall operation of external system 290. User interface 298 allows a user such as the physician or other caregiver or the patient to communicate with implantable medical device 210. In one embodiment, in response to each detection of a low energy level by battery status monitor 236, an alarm signal or warning message is produced and transmitted to external system 290 for presentation by user interface 298. In response, the user issues the user command that initiates a process of recharging rechargeable battery 232 or initiates a power transmission by power transmitter 294, which in turn initiates the process of recharging rechargeable battery 232.

Various specific embodiments of implantable medical device 210 and external system 290 and their components are discussed below as Examples 1-6. As those skilled in the art will understand after reading this document, these various specific embodiments can be combined in various ways and selectively utilized in system 100.

EXAMPLE 1

State of Charge Determination

Figure 3:
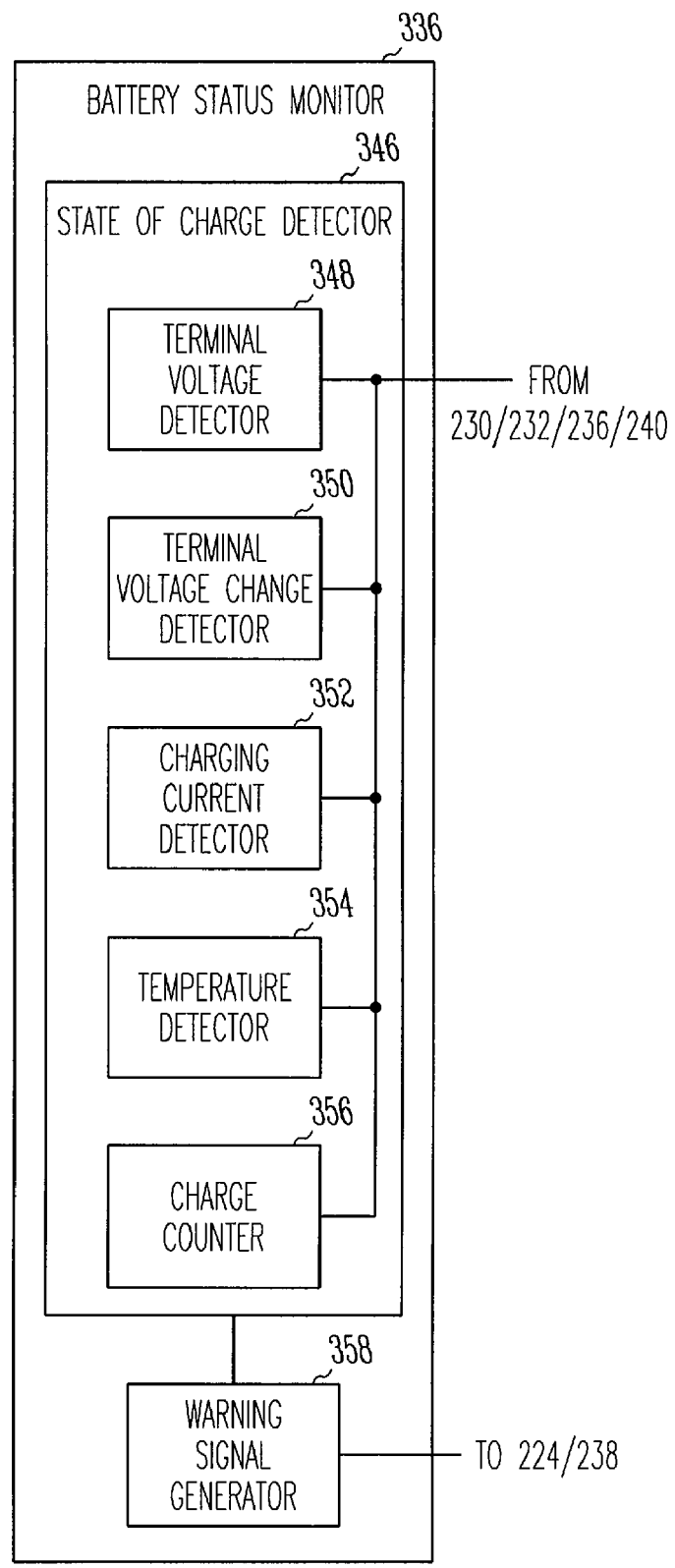
FIG. 3 is a block diagram illustrating an embodiment of a battery status monitor of the implantable medical device.

FIG. 3 is a block diagram illustrating an embodiment of a battery status monitor 336, which is a specific embodiment of battery status monitor 236. Battery status monitor 336 includes a state of charge detector 346 and a warning signal generator 358.

State of charge detector 346 detects a parameter indicative of the state of charge. State of charge represents the remaining charge in a battery relative to the full charge capacity of the battery, and is a measure of the energy level or content of the battery relative to the fully energy capacity of the battery. Examples of the parameter indicative of the state of charge include terminal voltage of the battery, impedance of the battery, charging current (non-constant) applied to the battery (if rechargeable), temperature of the battery, and discharging current of the battery. In one embodiment, as illustrated in FIG. 3, state of charge detector 346 includes a terminal voltage detector 348, a terminal voltage change detector 350, a charging current detector 352, a temperature detector 354, and a charge counter 356. In various other embodiments, state of charge detector 346 includes any one or more of terminal voltage detector 348, terminal voltage change detector 350, charging current detector 352, temperature detector 354, and charge counter 356. The state of charge is computed or estimated using one or more of parameters such as those detected by terminal voltage detector 348, terminal voltage change detector 350, charging current detector 352, temperature detector 354, and charge counter 356.

Figure 4:
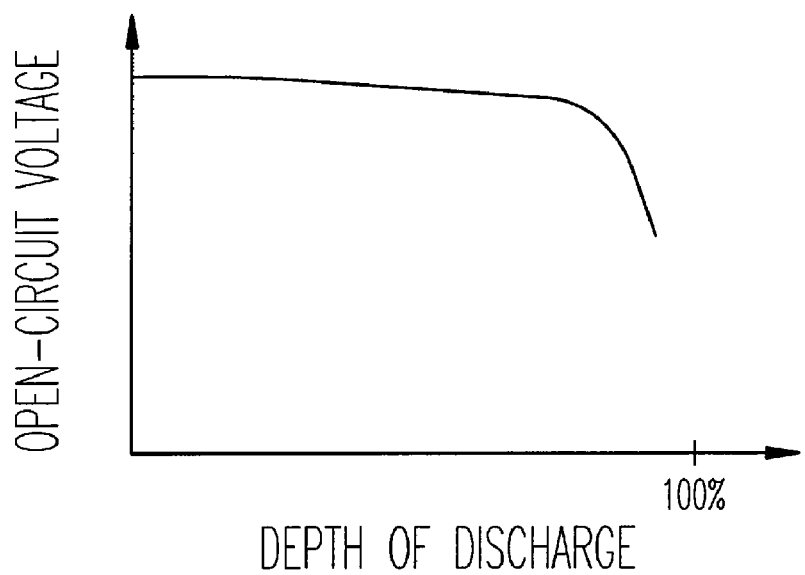
FIG. 4 is a graph illustrating a voltage characteristic of a rechargeable battery.

Terminal voltage detector 348 detects a terminal voltage being a voltage across the two terminals of a battery. FIG. 4 shows a graph showing the terminal voltage (open-circuit voltage) of a battery as a function of depth of discharge of the battery. This function allows for state of charge estimation using the terminal voltage of the battery. In various embodiments, the terminal voltage of rechargeable battery 232 is used to indicate the state of charge for the purpose of starting and stopping a process of recharging.

Figure 5:
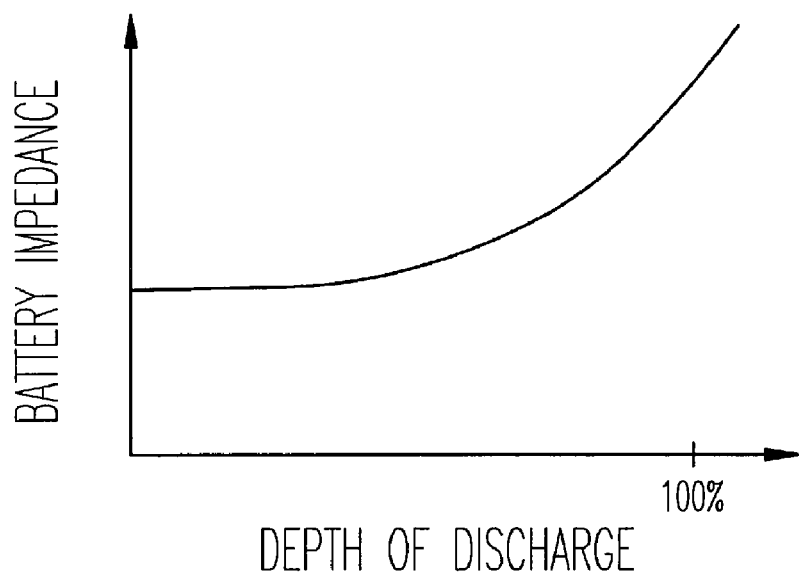
FIG. 5 is a graph illustrating an impedance characteristic of the rechargeable battery.

Terminal voltage change detector 350 detects a change in the terminal voltage that is indicative of the impedance of a battery. FIG. 5 shows a graph illustrating the impedance characteristic of a battery. The battery impedance starts from a non-zero impedance when fully charged and increases as the battery is discharged. With a known load, the impedance is represented by the change in the terminal voltage. The impedance characteristic as illustrated in FIG. 5 allows for state of charge estimation using the impedance of a battery. In various embodiments, the change in the terminal voltage is used to indicate the state of charge of rechargeable battery 232 for the purpose of starting and stopping the process of recharging. In various other embodiments, the change in the terminal voltage of a battery is used to indicate an unintended source of power consumption such as internal battery shorts and external circuit defects.

Charging current detector 352 detects a charging current applied to recharge rechargeable battery 232. A charging current with a particularly high amplitude leads to overcharging, which in turn causes adverse battery performance, thermal runaway, battery destruction, and venting. Thus, when the charging current exceeds a safety threshold, the process of recharging is to be terminated.

Temperature detector 354 detects the temperature of a battery. In addition to being a parameter indicative of the state of charge, the temperature is also a safety indication. An abnormally high temperature indicates that an adverse event has occurred and that an ongoing recharging process is to be terminated.

Charge counter 356 measures charging or discharging current. The total useable capacity of a battery is calculated using the charging or discharging current and time. This provides the most accurate measure of the state of charge.

In an alternative embodiment, the strength of a signal transmitted from implantable medical device 210 is detected by external system 290 to indicate the state of charge of a battery in implantable medical device 210. For example, when the signal is a radio-frequency electrical signal, the amplitude of the signal indicates the voltage supply level at implant telemetry circuit 224. The voltage supply level is in turn an indication of the state of charge of the battery providing energy to implant telemetry circuit 224.

Warning signal generator 358 produces one or more warning signals, such an alarm signal and a signal carrying a warning message, based on the detected parameter indicative of the state of charge. Such warning signals inform the user of a need to recharge a rechargeable battery and/or an end-point of battery life.

EXAMPLE 2

Dual-Phase Recharging

Figure 6:
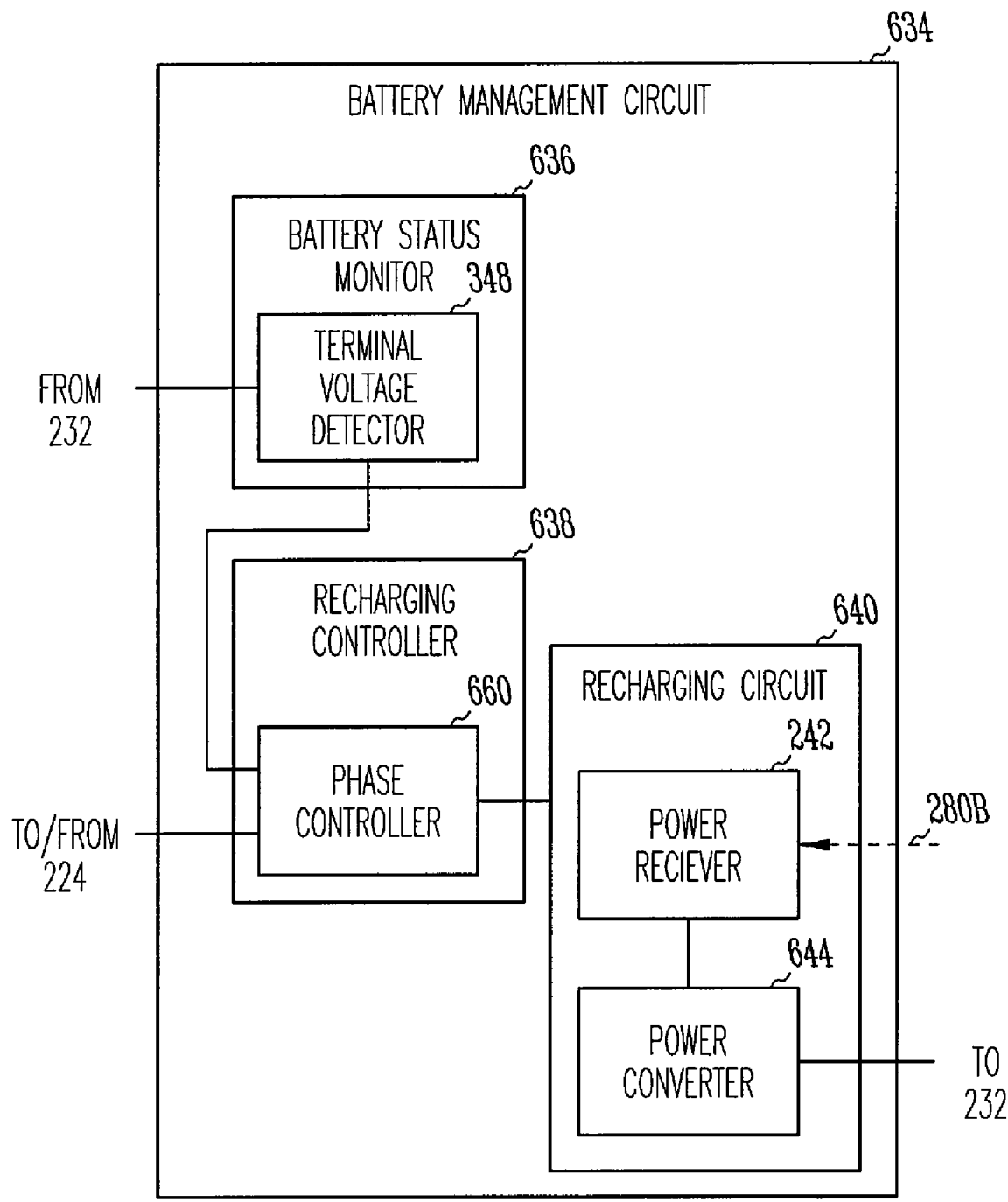
FIG. 6 is a block diagram illustrating an embodiment of a battery management circuit of the implantable medical device providing for recharging of a rechargeable battery.

FIG. 6 is a block diagram illustrating an embodiment of a battery management circuit 634, which is a specific embodiment of battery management circuit 234. Battery management circuit 634 includes a battery status monitor 636, a recharging controller 638, and a recharging circuit 640.

Battery status monitor 636 is a specific embodiment of battery status monitor 236 and monitors a parameter indicative of state of charge of rechargeable battery 232. In one embodiment, as illustrated in FIG. 6, battery status monitor 636 includes terminal voltage detector 348 to measure the terminal voltage of rechargeable battery 232. Recharging controller 638 is a specific embodiment of recharging controller 238 and includes a phase controller 660. Phase controller 660 initiates a fast-charge phase in response to a recharging command. Examples of the recharging command include a user command transmitted from external system 290 and a signal indicative of receipt of power-transmission signal. When the terminal voltage of rechargeable battery 232 rises to a predetermined phase-switch threshold, phase controller 660 switches the fast-charge phase to a trickle-charge phase. When the terminal voltage of rechargeable battery 232 reaches a predetermined end-of-charge threshold, phase controller 660 terminates the trickle-charge phase. Recharging circuit 640 is a specific embodiment of recharging circuit 240 and produces a constant-current signal for recharging rechargeable battery 232 during the fast-charge phase and a constant-voltage signal for recharging rechargeable battery 232 during the trickle-charge phase. Recharging circuit 640 includes power receiver 242 and a power converter 644. Power converter 644 converts the power-transmission signal received by power receiver 242 to the constant-current signal during the fast-charge phase and to the constant-voltage signal during the trickle-charge phase.

Figure 7:
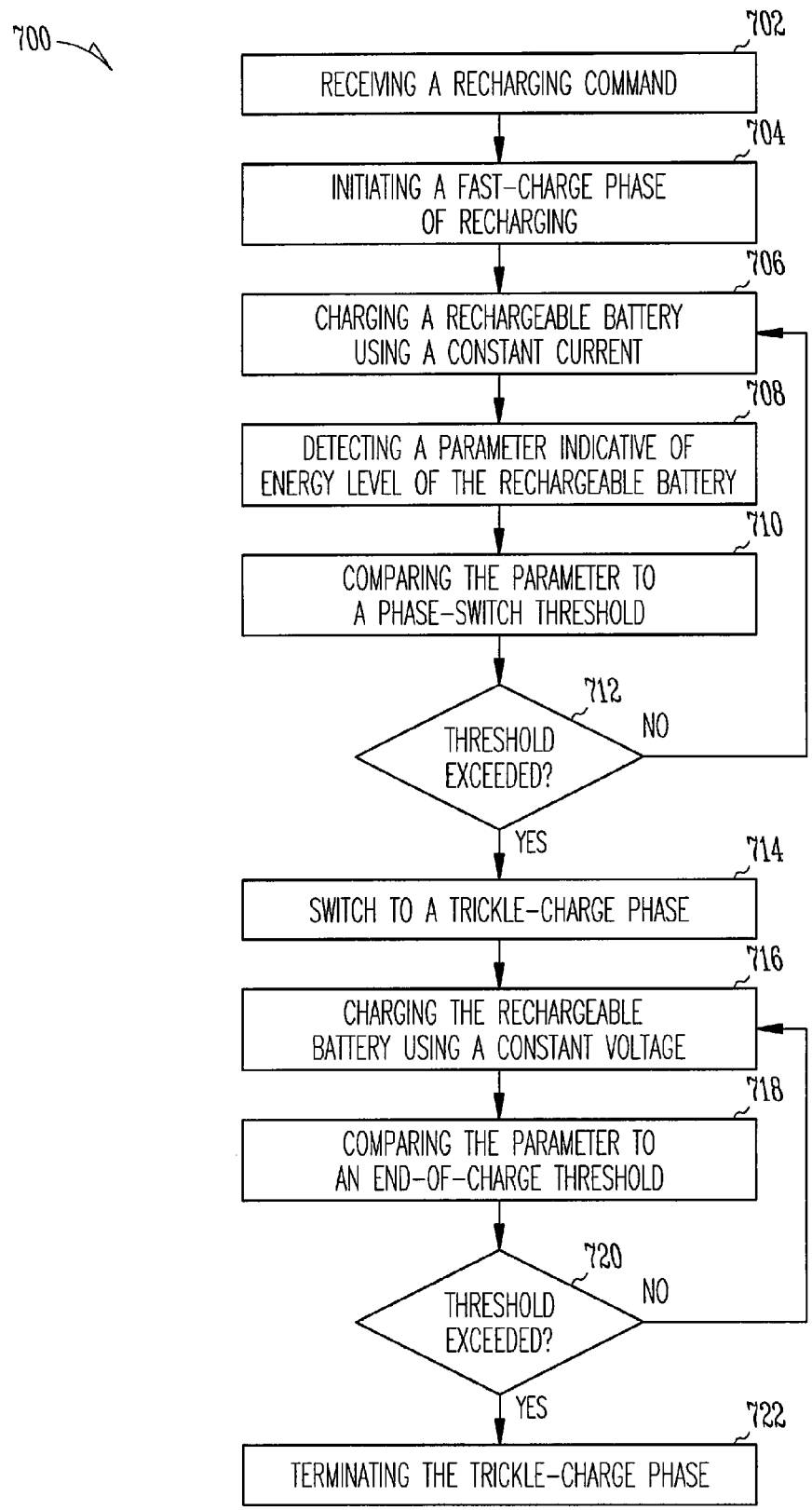
FIG. 7 is a flow chart illustrating an embodiment of a method for controlling a process of recharging a rechargeable battery in an implantable medical device.

FIG. 7 is a flow chart illustrating an embodiment of a method 700 for controlling recharge of a rechargeable battery in an implantable medical device. In one embodiment, method 700 is performed by battery management circuit 634.

A recharging command is received at 702. In one embodiment, the recharging command is issued by the user to initiate a process of recharging the rechargeable battery. In another embodiment, the recharging command is a signal indicating that the implantable medical device has received a power-transmission signal that carries the energy for recharging the rechargeable battery. In response to the recharging command, a fast-charge phase of recharging is initiated at 704. The rechargeable battery is charged using a constant current during the fast-charge phase at 706. A parameter indicative of energy level of the rechargeable battery is detected at 708. The parameter is compared to a phase-switch threshold at 710. If the parameter exceeds the phase-switch threshold at 712, the fast-charge phase is switched to a trickle-charge phase at 714. The rechargeable battery is charged using a constant voltage during the trickle-charge phase at 716. The parameter indicative of energy level of the rechargeable battery is compared to an end-of-charge threshold at 718. If the parameter exceeds the end-of-charge threshold at 720, the trickle-charge phase is terminated at 722, and this concludes the recharging process initiated by the recharging command.

EXAMPLE 3

Use of Rechargeable Battery as Effective Non-Rechargeable Battery

Figure 8:
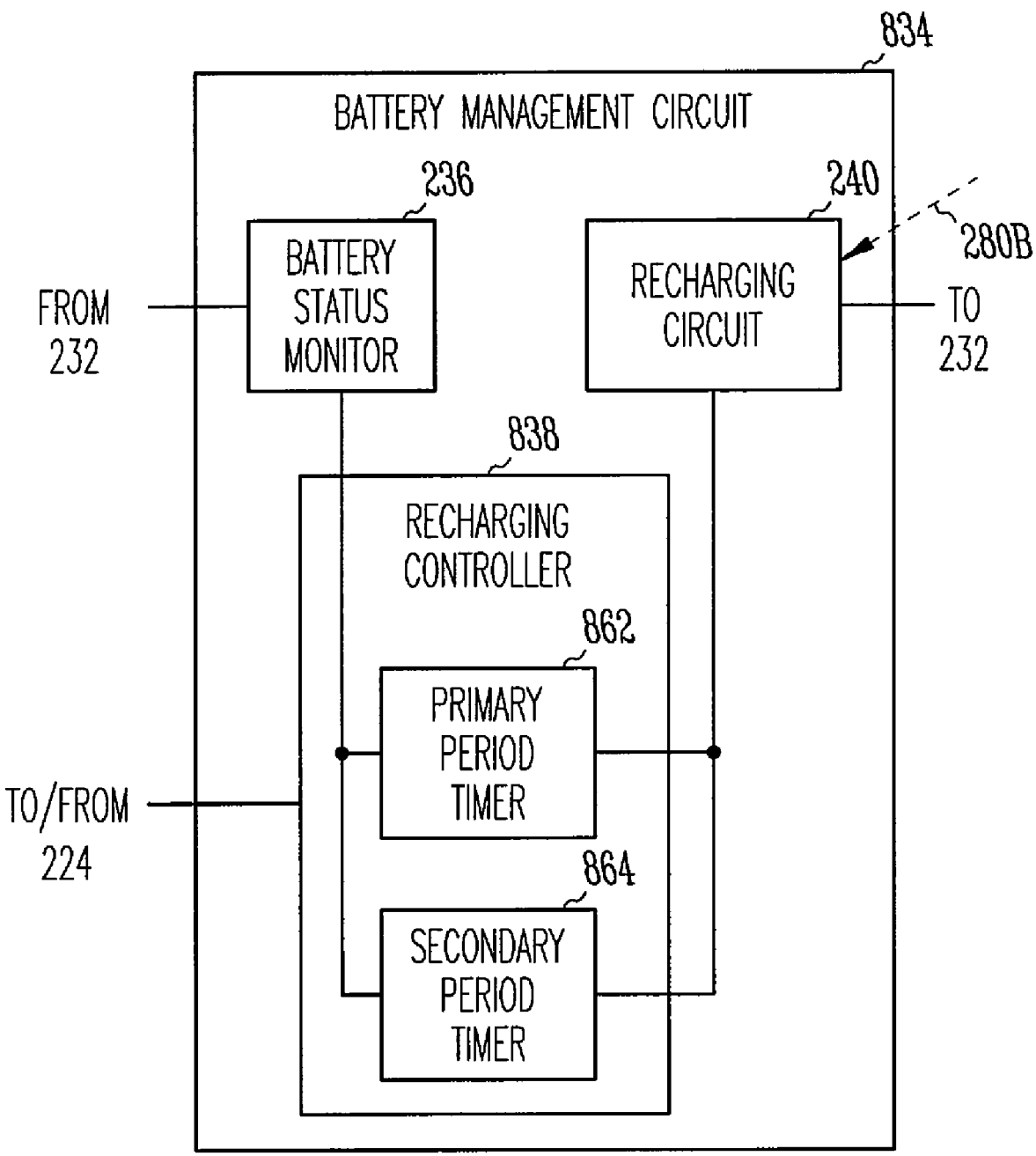
FIG. 8 is block diagram illustrating another embodiment of the battery management circuit of the implantable medical device.

FIG. 8 is block diagram illustrating an embodiment of a battery management circuit 834, which is a specific embodiment of battery management circuit 234. Battery management circuit 834 includes battery status monitor 236, recharging circuit 240, and a recharge controller 838.

Recharging controller 838 is a specific embodiment of recharging controller 238 and includes a primary period timer 862 and a secondary period timer 864. Primary period timer 862 times a primary period during which rechargeable battery 232 is not recharged. Secondary period timer 864 times a secondary period during which rechargeable battery 232 is recharged periodically or as needed. Recharging controller 838 suspends the recharging of rechargeable battery 232 during the primary period and controls the recharging of rechargeable battery 232 during the secondary period. Thus, during the primary period, rechargeable battery 232 is used as an effective non-rechargeable battery. The use of the primary duration eliminates the need for recharging the battery for a substantially long duration, such that the patient can enjoy the convenience of a non-rechargeable battery. The use of the secondary duration extends the longevity of implantable medical device 232 substantially beyond what is provided by a non-rechargeable battery.

In one embodiment, primary period timer 862 initiates the primary period in response to an initialization signal. The initialization signal indicates, for example, that the implantable medical device is initiated for use (such as at the time of implantation), that rechargeable battery is fully charged, or that the rechargeable battery is charged to a specified energy level (such as a specified terminal voltage). Secondary period timer 864 initiates the secondary period when the primary period expires. In another embodiment, secondary period timer 864 initiates the secondary period in response to the initialization signal. Primary period timer 862 initiates the primary period when the secondary period expires.

In one embodiment, primary period timer 862 times the primary period being a period having a predetermined duration. In another embodiment, primary period timer 862 stops the primary period when the energy level of rechargeable battery 232 drops below a discharge threshold. In another embodiment, primary period timer 862 stops the primary period either when the predetermined duration expires or when the energy level of rechargeable battery 232 drops below the discharge threshold, whichever occurs first. In one embodiment, the discharge threshold is user-programmable, such as using user interface 298 of external system 290. In one embodiment, the discharge threshold is approximately 10% of the battery capacity. In one embodiment, the energy level of the rechargeable battery 232 is represented by its terminal voltage, and the discharge threshold is given as a discharge threshold voltage level.

In one embodiment, rechargeable battery 232 is recharged during the secondary period to maintain a specified energy level for an extended longevity. Recharging controller 838 controls the process of recharging rechargeable battery 232 based on its energy level. A recharging process during the secondary period is initiated when the energy level of rechargeable battery 232 drops below the discharge threshold and terminated when the energy level of rechargeable battery 232 rises to a recharge threshold. In one embodiment, the recharge threshold is user-programmable, such as using user interface 298 of external system 290. In one embodiment, the recharge threshold is approximately 20% of the battery capacity. The energy level of rechargeable battery 232 swings between the discharge threshold and the recharge threshold. In one embodiment, the energy level of the rechargeable battery 232 is represented by its terminal voltage, and the recharge threshold is given as a recharge threshold voltage level.

In one embodiment, rechargeable battery 232 is recharged during the secondary period to maintain a minimum energy level for a specified longevity. Recharging controller 838 controls the recharging of the rechargeable battery during the secondary period based on the specified longevity of implantable medical device 210. In a specific embodiment, rechargeable battery 232 is recharged periodically during the secondary period. The duration of each recharging process is determined using specified longevity of implantable medical device 210.

Figure 9:
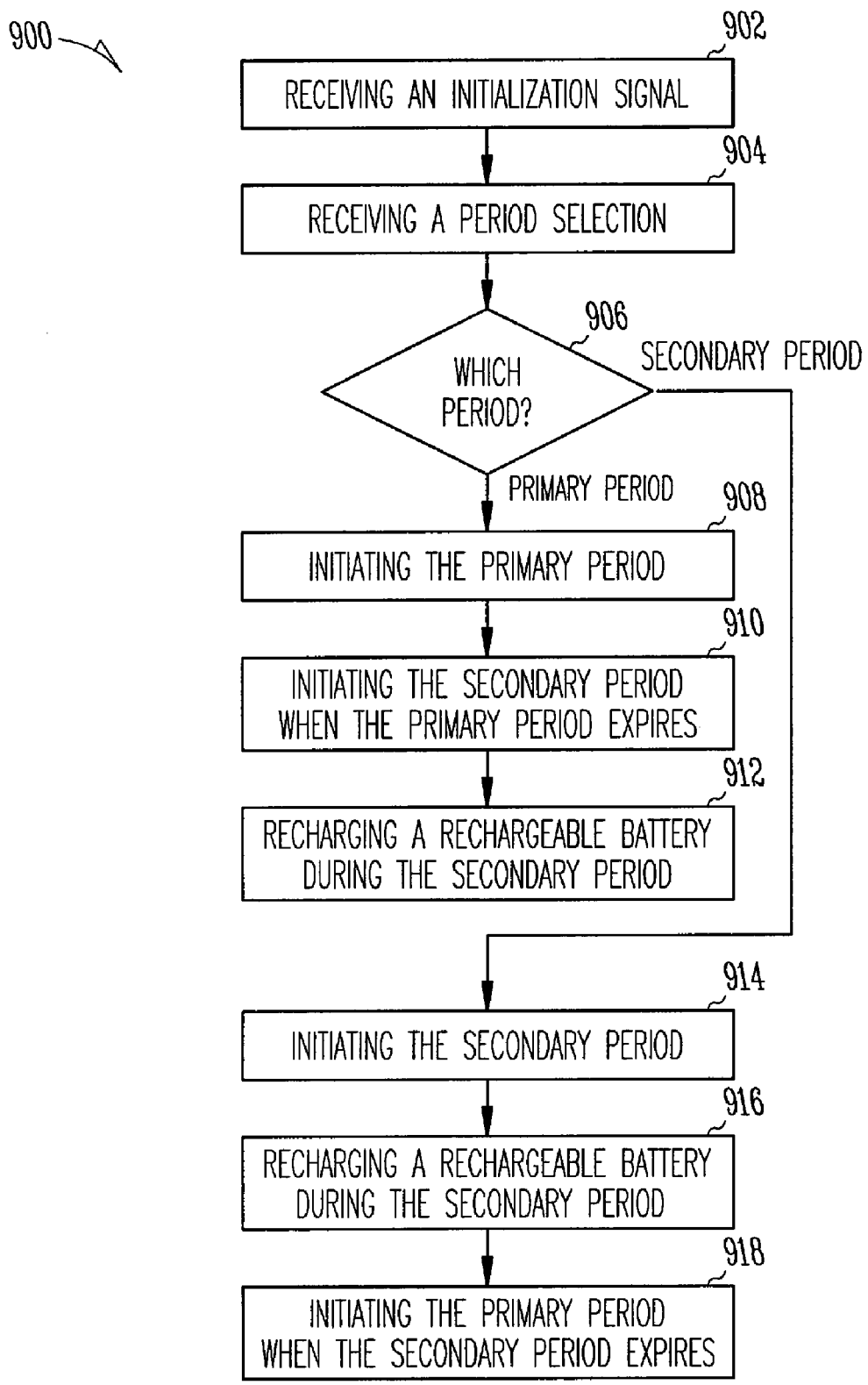
FIG. 9 is a flow chart illustrating an embodiment of a method for timing a process of recharging a rechargeable battery in an implantable medical device.

FIG. 9 is a flow chart illustrating an embodiment of a method 900 for timing recharging of a rechargeable battery in an implantable medical device. Method 900 uses a primary period during which the rechargeable battery is not recharged and a secondary period during which the rechargeable battery is recharged periodically or as needed. In one embodiment, the method is performed by battery management circuit 834.

An initialization signal is received at 902, when the implantable medical device is initiated for use, when the rechargeable battery is fully charged, or when the rechargeable battery is charged to a specified energy level. A selection of one of the primary and secondary periods is received at 904. This selection defines which of the primary and secondary periods is initiated first in response to the initialization signal.

If the primary period is selected as 906, the primary period is initiated in response to the initialization signal at 908. The secondary period is initiated when the primary period expires at 910. The rechargeable battery is recharged periodically or as needed during the secondary period at 912.

If the secondary period is selected as 906, the secondary period is initiated in response to the initialization signal at 914. The rechargeable battery is recharged periodically or as needed during the secondary period at 916. The primary period is initiated when the secondary period expires at 918.

In one embodiment, the primary period expires after being initiated for a predetermined duration. In another embodiment, the primary period expires when the energy level of the rechargeable battery drops below a discharge threshold. In another embodiment, the primary period expires either after being initiated for the predetermined duration or when the energy level of the rechargeable battery drops below the discharge threshold, whichever occurs first. In one embodiment, the discharge threshold is user-programmable.

Figure 10:
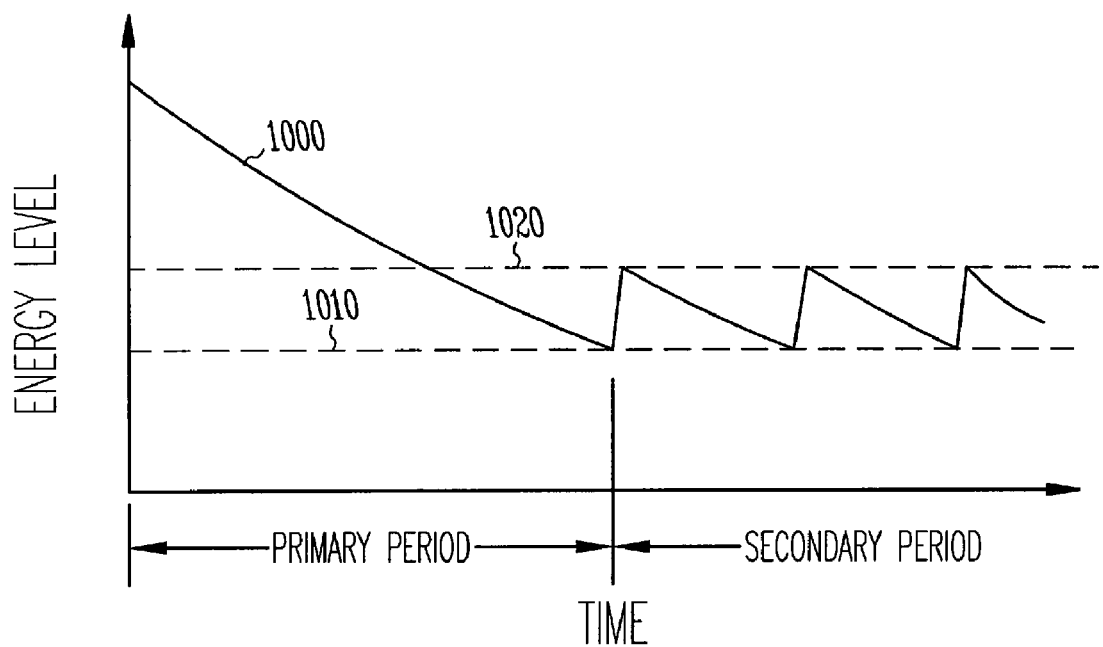
FIG. 10 is a graph illustrating the energy level of a rechargeable battery as a function of depth of charge in a specific embodiment of the method of FIG. 9.

In one embodiment, step 912 is performed to maintain a specified energy level. As illustrated in FIG. 10, an energy level 1000 of the rechargeable drops to a discharge threshold 1010 at the end of the primary period. During the secondary period, each recharging process starts when the energy level of the rechargeable battery drops below discharge threshold 1010, and stops when the energy level of the rechargeable battery rises to a recharge threshold 1020. This embodiment allows for an infinite longevity of the implantable medical device.

Figure 11:
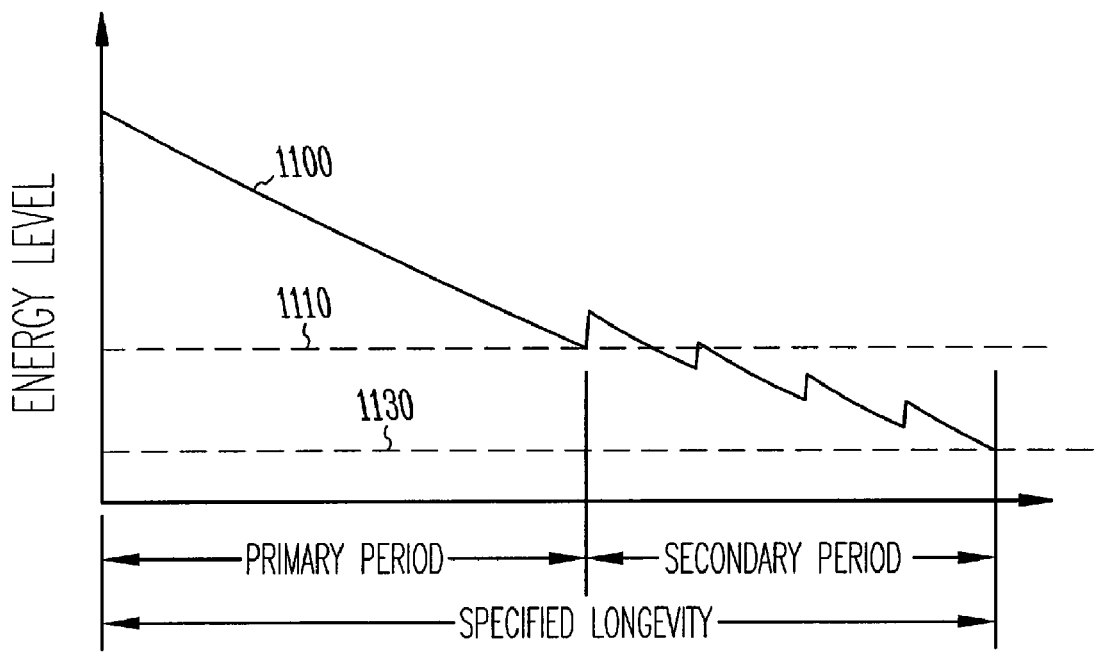
FIG. 11 is a graph illustrating the energy level of the rechargeable battery as a function of depth of charge in another specific embodiment of the method of FIG. 9.

In another embodiment, step 912 is performed for a specified longevity of the implantable medical device. As illustrated in FIG. 11, an energy level 1100 of the implantable medical device drops to a discharge threshold 1110 at the end of the primary period. During the secondary period, the rechargeable battery is recharged periodically to keep energy level 1100 above an end-point threshold 1130. The second period expires at the end of the specified longevity of the implantable medical device. This embodiment allows minimum time spend on recharging the rechargeable battery in the implantable medical device.

EXAMPLE 4

Power Source with Non-Rechargeable and Rechargeable Batteries

Figure 12:
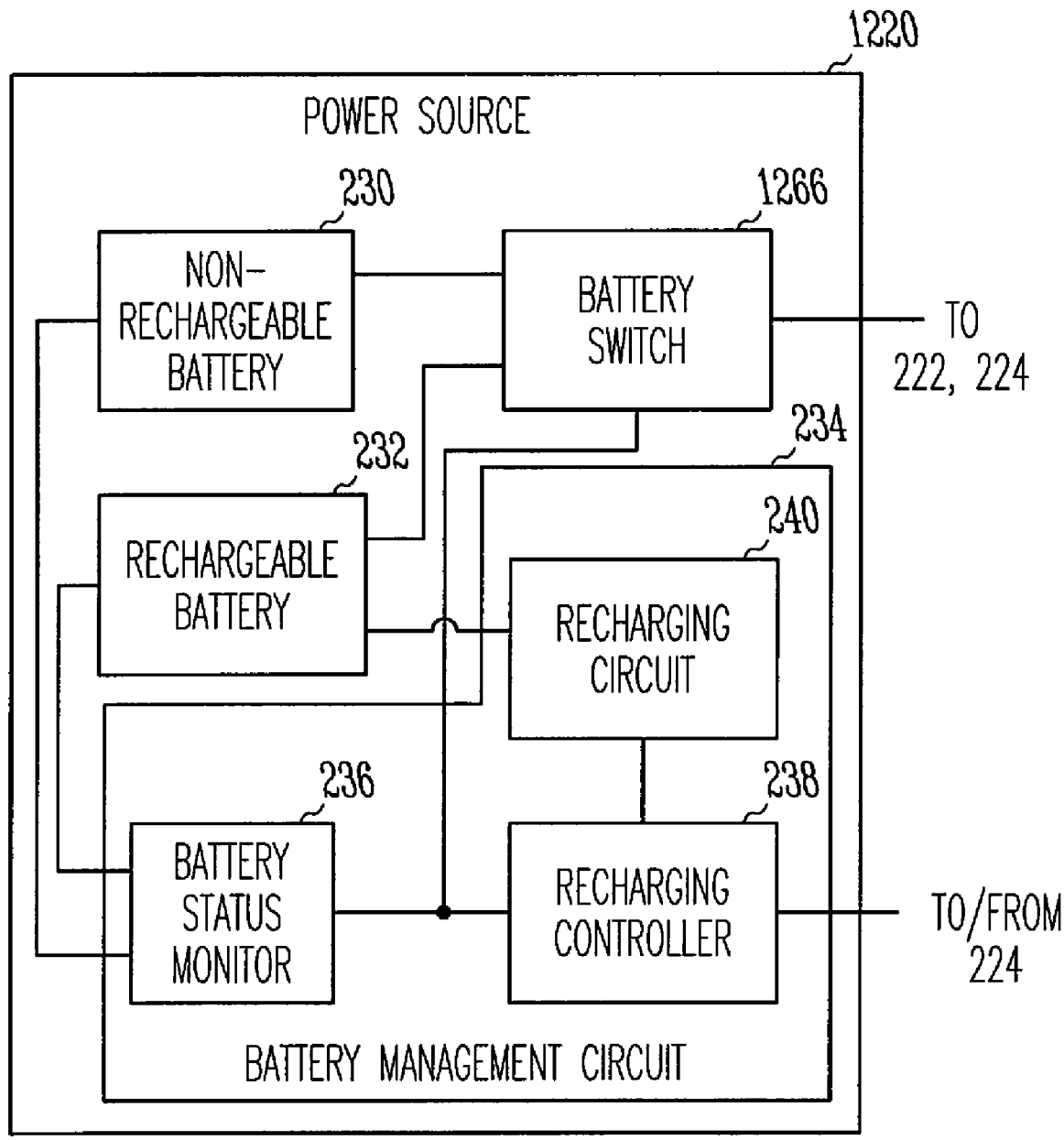
FIG. 12 is block diagram illustrating an embodiment of a power source of the implantable medical device including rechargeable and non-rechargeable batteries.

FIG. 12 is block diagram illustrating an embodiment of a power source 1220, which is a specific embodiment of power source 220. Power source 1220 includes non-rechargeable battery 230, rechargeable battery 232, battery management circuit 234, and a battery switch 1266.

Battery switch 1266 connects one of rechargeable battery 232 and non-rechargeable battery 230 to feature circuit 222 and implant telemetry circuit 224. That is, battery switch 1266 is used to select which of rechargeable battery 232 and non-rechargeable battery 230 is used to power implantable medical device 210. In one embodiment, battery switch 1266 is programmable for selecting one of rechargeable battery 232 and non-rechargeable battery 230 as the main energy source of implantable medical device 210 and the remaining one as the supplemental or back-up energy source of implantable medical device 210.

In one embodiment, non-rechargeable battery 230 is used as the main energy source, and rechargeable battery 232 is used as a supplemental or back-up energy source. When the energy level of non-rechargeable battery 230 is above a predetermined threshold, battery switch 1266 provides electrical connection between non-rechargeable battery 230 and the powered circuits including feature circuit 222 and implant telemetry circuit 224. When the energy level of non-rechargeable battery 230 is not above the predetermined threshold, battery switch 1266 provides electrical connection between rechargeable battery 232 and the powered circuits.

In an alternative embodiment, rechargeable battery 232 is used as the main energy source, and non-rechargeable battery 230 is used as a supplemental or back-up energy source. When the energy level of rechargeable battery 232 is above a predetermined threshold, battery switch 1266 provides electrical connection between rechargeable battery 232 and the powered circuits including feature circuit 222 and implant telemetry circuit 224. When the energy level of the rechargeable battery is not above the predetermined threshold, battery switch 1266 provides electrical connection between non-rechargeable battery 230 and the powered circuits.

Figure 13:
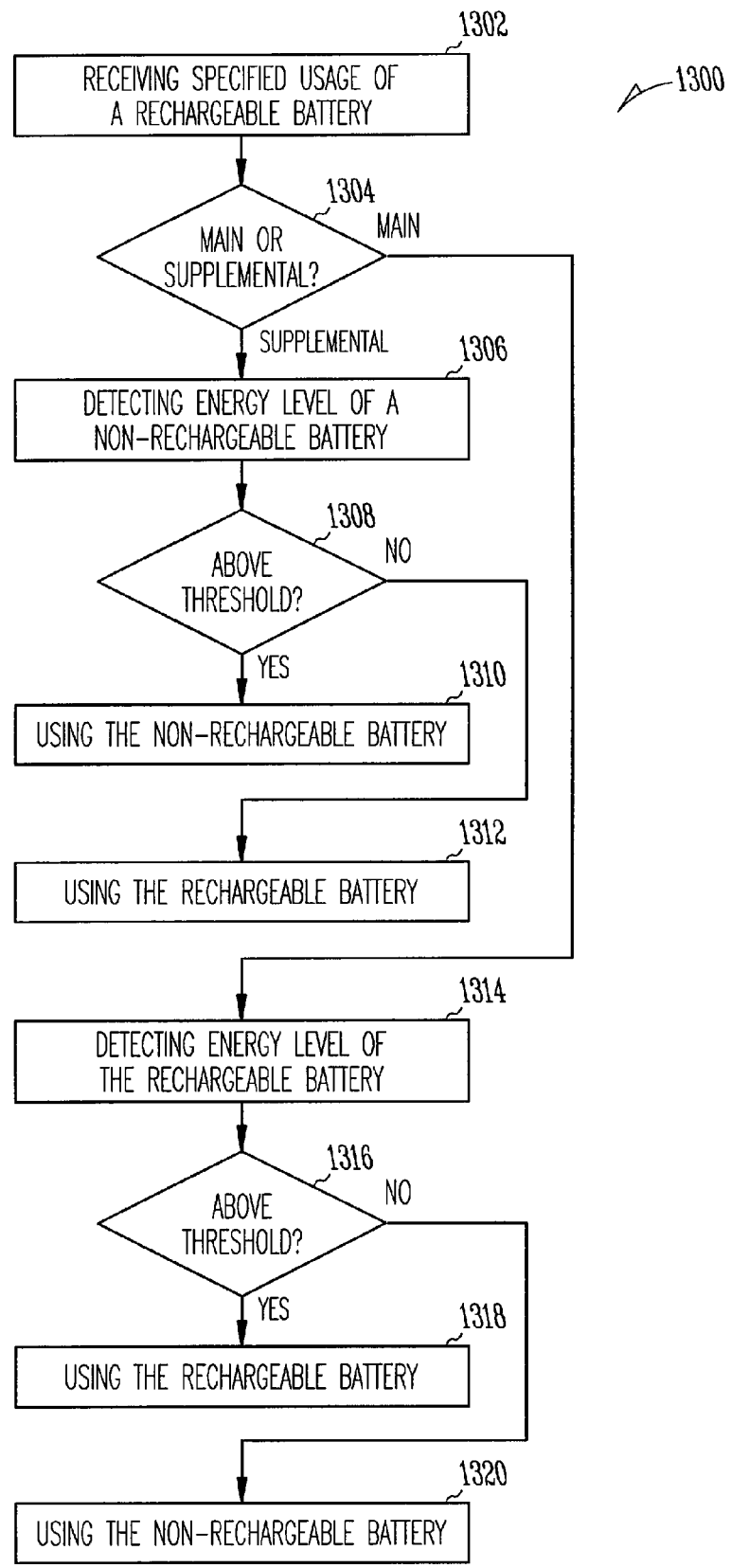
FIG. 13 is a flow chart illustrating an embodiment of a method for power management in an implantable medical device powered by rechargeable and non-rechargeable batteries.

FIG. 13 is a flow chart illustrating an embodiment of a method 1300 for power management in an implantable medical device powered by rechargeable and non-rechargeable batteries. In one embodiment, method 1300 is performed by power source 1220.

A specified usage of the rechargeable battery is received at 1302. The specific usage is selected from use as one of the main energy source and the supplemental energy source of the implantable medical device.

If the rechargeable battery is specified as the supplemental energy source at 1304, the energy level of the non-rechargeable battery is detected at 1306. If the energy level of the non-rechargeable battery is above a predetermined threshold at 1308, the implantable medical device is powered using the non-rechargeable battery at 1310. If the energy level of the non-rechargeable battery is not above a predetermined threshold at 1308, the implantable medical device is powered using the rechargeable battery at 1312.

If the rechargeable battery is specified as the main energy source at 1304, the energy level of the rechargeable battery is detected at 1314. If the energy level of the rechargeable battery is above a predetermined threshold at 1316, the implantable medical device is powered using the rechargeable battery at 1318. If the energy level of the rechargeable battery is not above a predetermined threshold at 1316, the implantable medical device is powered using the non-rechargeable battery at 1320.

EXAMPLE 5

Implantable Sensor Module Powered by Rechargeable Battery

Figure 14:
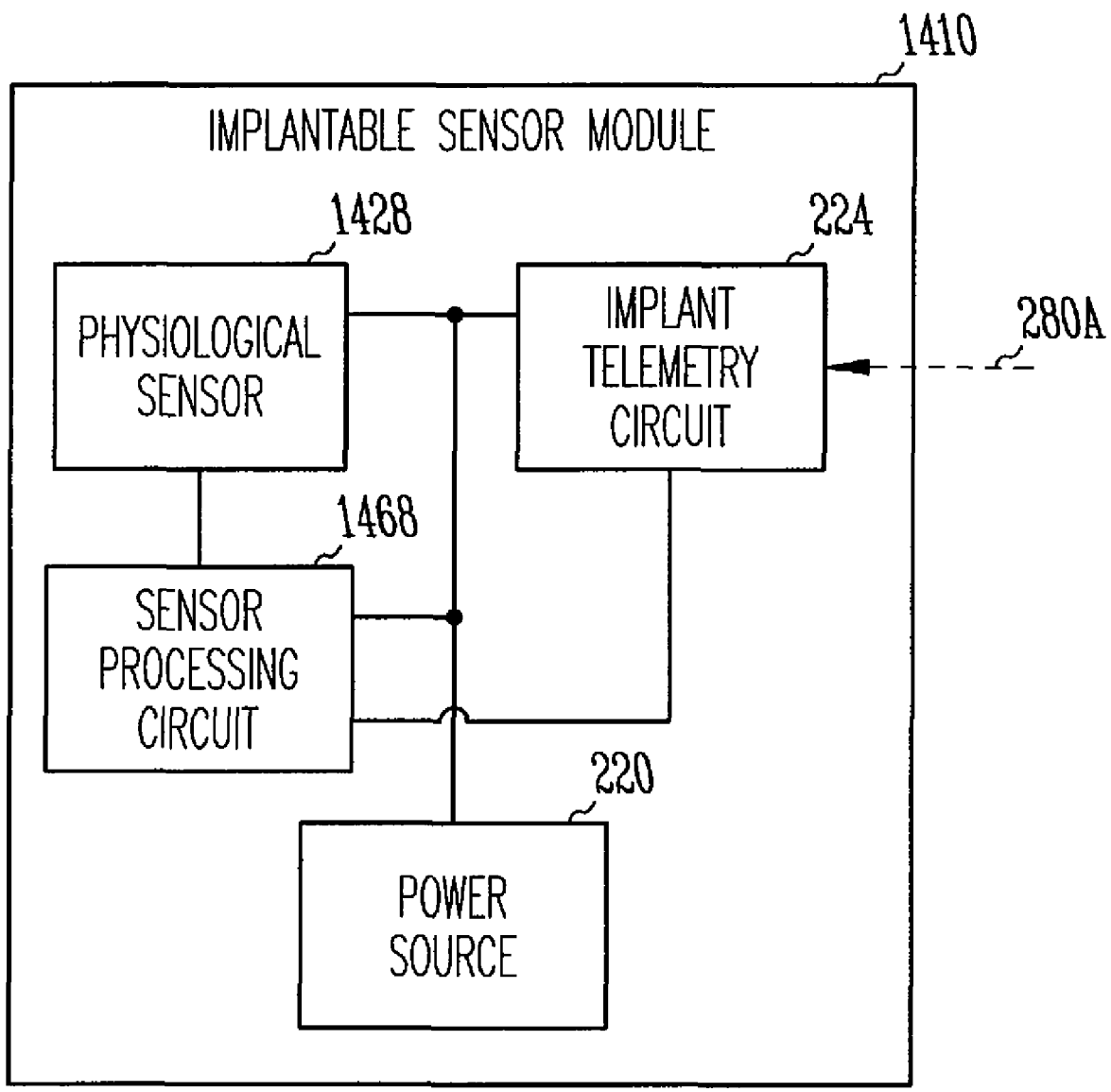
FIG. 14 is a block diagram illustrating an embodiment of an implantable sensor module powered by a rechargeable battery.

FIG. 14 is a block diagram illustrating an embodiment of an implantable sensor module 1410, which is a specific embodiment of implantable medical device 210. Implantable sensor module 1410 includes a physiological sensor 1428, a sensor processing circuit 1468, power source 220, and implant telemetry circuit 224. In one embodiment, implantable sensor module 1410 is part of an implantable system that includes two or more devices implanted in the same patient. The devices communicate with each other via telemetry. An example of such an implantable system is discussed in U.S. patent application Ser. No. 10/888,956, "METHOD AND APPARATUS OF ACOUSTIC COMMUNICATION FOR IMPLANTABLE MEDICAL DEVICE," filed Jul. 9, 2004, assigned to Cardiac Pacemakers, Inc., which is incorporated herein by reference in its entirety.

Physiological sensor 1428 senses a physiological signal. The physiological signal is sensed for one or more diagnostic, monitoring, or therapeutic purposes. In one embodiment, physiological sensor 1428 includes a pressure sensor that senses a pressure signal indicative of a blood pressure. Other examples of physiological sensor 1428 include a biopotential sensor, an impedance sensor, a chemical sensor, an accelerometer, a microphone, a temperature sensor, and a posture sensor. Examples of the physiological signal include electrograms, heart sounds or signals indicative of heart sounds, neural signals, activity level signals, pressure signals, impedance signals, respiratory signals, signals indicative of metabolic level, signals indicative of blood glucose level, signals indicative of blood oxygen saturation, signals indicative of body posture. Sensor processing circuit 1468 processes the sensed physiological signal for transmission by implantable telemetry circuit 224. In one embodiment, sensor processing circuit 1468 conditions the sensed physiological signal for digitization and produces binary data representative of the sensed physiological signal. In one embodiment, sensor processing circuit 1468 further derives one or more parameters from the sensed physiological signal and produces binary data representative of the one or more parameters. Implant telemetry circuit 224 transmits the data representative of the sensed physiological signal and/or the one or more parameters to external system 290 or another implantable device.

EXAMPLE 6

Ultrasonic Energy Transmission

Figure 15:
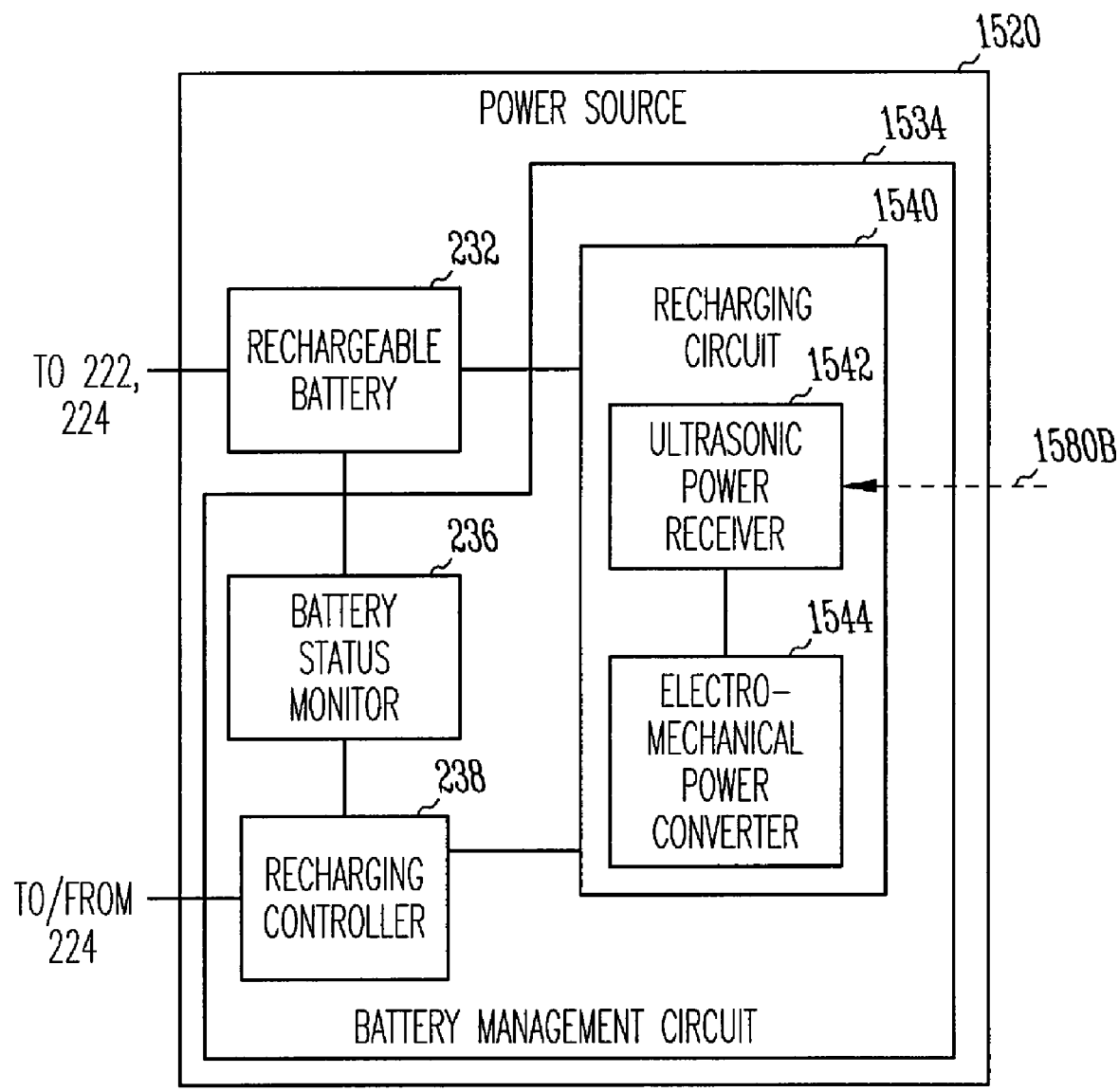
FIG. 15 is a block diagram illustrating another embodiment of the power source of the implantable medical device.

FIG. 15 is a block diagram illustrating an embodiment of a power source 1520, which is a specific embodiment of power source 220. Power source 1520 includes rechargeable battery 232 and a battery management circuit 1534. An ultrasonic power-transmission link 1580B is utilized for transmitting the energy for recharging rechargeable battery 232. In one embodiment, power source 1520 is included as the power source 220 of implantable sensor module 1410.

Battery management circuit 1534 is a specific embodiment of battery management circuit 234 and includes battery status monitor 236, recharging controller 238, and a recharging circuit 1540. Recharging circuit 1540 includes an ultrasonic power receiver 1542 and an electromechanical power converter 1544. Ultrasonic power receiver 1542 receives an ultrasonic signal transmitted from external system 290 via ultrasonic power-transmission link 1580B. In one embodiment, ultrasonic power-transmission link 1580B is part of an integrated ultrasonic data-transmission and power-transmission link, and the ultrasonic signal is also modulated for data transmission. Electromechanical power converter 1544 converts the ultrasonic energy to electrical energy. In response to the received ultrasonic signal, electromechanical power converter 1544 oscillates and generates an oscillating electrical current. Recharging circuit 1540 converts the oscillating electrical current to a dc recharging current suitable for recharging rechargeable battery 232. The recharging current is given by:

$$I_{recharge-ave} = 4 \cdot C \cdot f \cdot (P_{peak} \cdot A - V_{bat} - V_{circuit}),$$

where $I_{recharge-ave}$ is the average recharge current, C is the capacitance of electromechanical power converter 1544, f is the frequency of the ultrasonic power-transmission signal, $P_{peak}$ is the peak ultrasound pressure applied to electromechanical power converter 1544, A is the efficiency of electromechanical power converter 1544, $V_{bat}$ is the voltage of rechargeable battery 232, and $V_{circuit}$ represents voltage loss due to inefficiency of recharging circuit 1540. In one embodiment, the frequency of the ultrasonic power-transmission signal is in a range between 38 kHz and 42 kHz, with approximately 40 kHz being a specific example. In one embodiment, electromechanical power converter 1544 includes a piezoelectric transducer.

Figure 16:
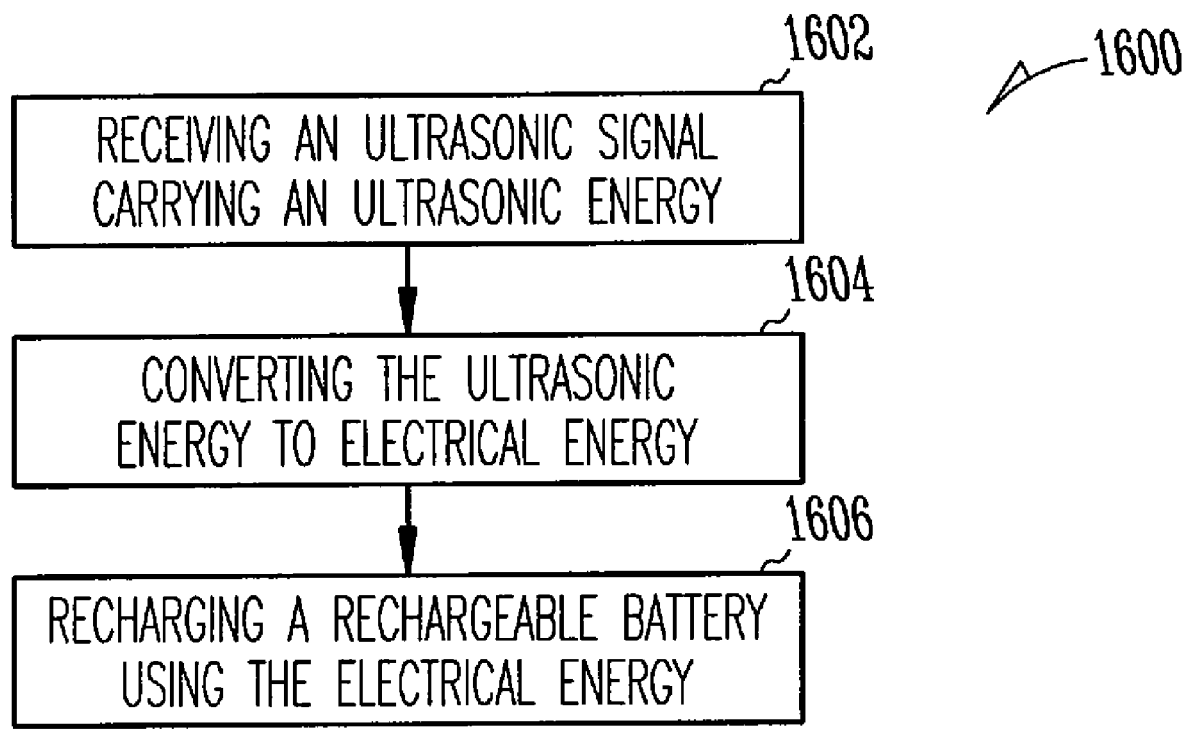
FIG. 16 is a flow chart illustrating an embodiment of a method for energy transmission for recharging a rechargeable battery in an implantable medical device.

FIG. 16 is a flow chart illustrating an embodiment of a method 1600 for ultrasonic power transmission for recharging a rechargeable battery in an implantable medical device.

An ultrasonic signal carrying an ultrasonic energy is received by the implantable medical device at 1602. In one embodiment, the ultrasonic signal is also utilized for transmitting data to the implantable medical device. The ultrasonic energy is converted to electrical energy at 1604. The rechargeable battery is recharged using the electrical energy at 1606. In one embodiment, the ultrasonic signal causes an electromechanical power converter such as a piezoelectric transducer to oscillate at the frequency of the ultrasonic signal, resulting in an oscillating electrical current at 1604. The oscillating electrical current is then converted to a dc current and regulated for recharging the rechargeable battery at 1606.

The feasibility of ultrasonic power transmission for recharging a rechargeable battery in an implantable medical device depends on the achievable efficiency of power transmission and conversion and the power consumption of the implantable medical device. In one embodiment, ultrasonic power transmission is utilized in implantable sensor module 1410 because of its relatively small power consumption.

In General

Various specific embodiments of components of implantable medical device 210 are discussed above as Examples 1-6. In general, each circuit element illustrated in FIG. 2 can be implemented using any of the specific embodiments of that element, including those discussed in this document, as long as the resulting combination of elements is appropriate as determined by those skilled in the art. For illustrative purposes, examples for such combination are presented below.

In one example, battery status monitor 236, such as illustrated in FIGS. 2, 8, 12, and 15, is implemented according to the discussion of its specific embodiment battery status monitor 336, which includes any one or more of terminal voltage detector 348, terminal voltage change detector 350, charging current detector 352, temperature detector 354, and charge counter 356.

In another example, recharging controller 238, such as illustrated in FIGS. 2, 12, and 15, is implemented as a combination of recharging controller 638 and recharging controller 838. That is, recharging controller 238 includes primary timer 862, secondary timer 864, and phase controller 660. During the secondary period timed by secondary period timer 864, the process of recharging rechargeable battery 232 includes the fast-charge phase and the trickle-charge phase as controlled by phase controller 660.

In another example, recharging circuit 240, such as illustrated in FIGS. 2, 8, and 12, as well as its specific embodiment recharging circuit 640 illustrated in FIG. 6, is implemented according to the discussion of its specific embodiment recharging circuit 1540. When ultrasonic power transmission is desirable and also capable of providing implantable medical device 210 with energy required for recharging rechargeable battery 232, recharging circuit 240 or 640 is implemented as recharging circuit 1540.

It is to be understood that the above detailed description, including Examples 1-6 and all other examples discussed above, is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system, comprising:
    an implantable medical device including a power source including:
        a rechargeable battery;
        a battery status monitor coupled to the rechargeable battery, the battery status monitor including a terminal voltage detector adapted to detect a terminal voltage of the rechargeable battery;
        a recharging controller coupled to the battery status monitor, the recharging controller adapted to control a process of recharging the rechargeable battery using the terminal voltage and including a phase controller, the process including a fast-charge phase and a trickle-charge phase, the phase controller adapted to initiate the fast-charge phase in response to a recharging command, to switch from the fast-charge phase to the trickle-charge phase when the terminal voltage reaches a predetermined phase-switch threshold voltage, and to terminate the trickle-charge phase when the terminal voltage reaches a predetermined end-of-charge threshold voltage; and
        a recharging circuit coupled to the recharging controller and the rechargeable battery, the recharging circuit including:
            a power receiver adapted to receive a power-transmission signal; and
            a power converter adapted to convert the power-transmission signal to a constant-current signal during the fast-charge phase and to a constant-voltage signal during the trickle-charge phase.

2. The system of claim 1, further comprising an external system communicatively coupled to the implantable medical device, and wherein the phase controller is adapted to initiate the fast-charge phase in response to a user command transmitted from the external system.

3. The system of claim 1, further comprising an external system communicatively coupled to the implantable medical device, the external system including a power transmitter to transmit the power-transmission signal to the implantable medical device, and wherein the phase controller is adapted to initiate the fast-charge phase in response to receipt of the power-transmission signal.

4. A method for operating an implantable medical device, the method comprising:
    detecting a terminal voltage of a rechargeable battery of the implantable medical device;
    controlling a process of recharging the rechargeable battery using the terminal voltage, the process including a fast-charge phase and a trickle-charge phase;
    receiving a recharging command;
    initiating the fast-charge phase in response to the recharging command;
    charging the rechargeable battery using a constant current during the fast-charge phase;
    switching from the fast-charge phase to the trickle-charge phase when the terminal voltage exceeds a predetermined phase-switch threshold voltage;
    charging the rechargeable battery using a constant voltage during the trickle-charge phase; and
    terminating the trickle-charge phase when the terminal voltage reaches a predetermined end-of-charge threshold voltage.

5. The method of claim 4, wherein receiving the recharge command comprises receiving a command initiating the process of recharging the rechargeable battery from a user.

6. The method of claim 4, wherein receiving the recharge command comprises receiving a signal indicating that the implantable medical device has received a power-transmission signal that carries energy for recharging the rechargeable battery.

7. A system, comprising:
    an implantable medical device including a power source including:
        a rechargeable battery;
        a recharging circuit coupled to the rechargeable battery, the recharging circuit adapted to recharge the rechargeable battery; and
        a recharging controller coupled to the recharging circuit, the recharging controller adapted to suspend the recharging of the rechargeable battery during a primary period and to control the recharging of the rechargeable battery during a secondary period, the recharging controller including:
            a primary period timer adapted to initiate the primary period in response to an initiation signal; and
            a secondary period timer adapted to initiate the secondary period when the primary period expires.

8. The system of claim 7, wherein the primary period timer is adapted to time a predetermined duration as the primary period.

9. The system of claim 7, wherein the power source comprises a battery status monitor coupled to the rechargeable battery, the battery status monitor adapted to detect an energy level of the rechargeable battery, and wherein the recharging controller is adapted to control the recharging of the rechargeable battery using the energy level.

10. The system of claim 9, wherein the primary period timer is adapted to stop the primary period when the energy level drops below a discharge threshold.

11. The system of claim 9, wherein the primary period timer is adapted to stop the primary period when a predetermined duration expires or when the energy level drops below a discharge threshold, whichever occurs first.

12. The system of claim 9, wherein the recharging controller is adapted to control the recharging of the rechargeable battery during the secondary period using the energy level.

13. The system of claim 12, wherein the recharging controller is adapted to initiate a recharging process during the secondary period when the energy level drops below a discharge threshold and to terminate that recharging process when the energy level rises to a recharge threshold.

14. The system of claim 9, wherein the battery status monitor comprises means for detecting a parameter indicative of a state of charge of the rechargeable battery.

15. The system of claim 7, wherein the recharging controller is adapted to control the recharging of the rechargeable battery during the secondary period based on a specified longevity of the implantable medical device.

16. The system of claim 15, wherein the recharging controller is adapted to initiate a recharging process periodically during the secondary period.

17. A method for operating an implantable medical device, the method comprising:
  initiating a primary period in response to an initiation signal indicating that the implantable medical device is initiated for use;
  initiating a secondary period in response to a termination of the primary period, the secondary period extending longevity of the implantable medical device after the termination of the primary period;
  suspending recharging of a rechargeable battery of the implantable medical device during the primary period;
  detecting an energy level of the rechargeable battery; and
  controlling the recharging of the rechargeable battery using the energy level during the secondary period.

18. The method of claim 17, comprising:
  timing a predetermined duration; and
  terminating the primary period when the predetermined duration expires.

19. The method of claim 17, comprising terminating the primary period when the energy level drops below a discharge threshold.

20. The method of claim 17, wherein control the recharging of the rechargeable battery during the secondary period comprises:
  initiating a recharging process during the secondary period when the energy level drops below a discharge threshold; and
  terminating that recharge process when the energy level rises to a recharge threshold.

21. The method of claim 17, wherein controlling the recharging of the rechargeable battery during the secondary period comprises controlling the recharging of the rechargeable battery based on a specified longevity of the implantable medical device.

22. The method of claim 21, wherein controlling the recharging of the rechargeable battery during the secondary period comprises initiating a recharging process periodically during the secondary period.

23. A system, comprising:
  an implantable medical device including:
    a feature circuit including one or more of a sensing circuit to sense one or more physiological signals and an electrical stimulation circuit to deliver electrical stimulation; and
    a power source adapted to provide power to the feature circuit, the power source including:
      a rechargeable battery;
      a non-rechargeable battery;
      a battery status monitor coupled to the rechargeable battery and the non-rechargeable battery, the battery status monitor adapted to detect at least one of a first energy level of the rechargeable battery and a second energy level of the non-rechargeable battery; and
      a battery switch coupled between the feature circuit and the power source, the battery switch adapted to selectively provide an electrical connection between the feature circuit and one of the rechargeable battery and the non-rechargeable battery using at least one of the first energy level and the second energy level.

24. The system of claim 23, wherein the battery switch is programmed to provide the electrical connection between the feature circuit and the non-rechargeable battery while the second energy level is above a predetermined threshold and to provide the electrical connection between the feature circuit and the rechargeable battery while the second energy level is not above a predetermined threshold.

25. The system of claim 23, wherein the battery switch is programmed to provide the electrical connection between the feature circuit and the rechargeable battery while first energy level is above a predetermined threshold and to provide the electrical connection between the feature circuit and the non-rechargeable battery while the first energy level is not above a predetermined threshold.

26. The system of claim 23, wherein the battery status monitor comprises means for detecting a parameter indicative of a state of charge of each of the rechargeable battery and the non-rechargeable battery.

27. The system of claim 26, wherein the battery status monitor comprises a warning signal generator adapted to produce one or more warning signals using the parameter indicative of the state of charge.

28. A method for operating an implantable medical device including a rechargeable battery and a non-rechargeable battery, the method comprising:
  detecting at least one of a first energy level of the rechargeable battery and a second energy level of the non-rechargeable battery; and
  selecting one of the rechargeable battery and the non-rechargeable battery to power the implantable medical device using at least one of the first energy level and the second energy level.

29. The method of claim 28, comprising:
  powering the implantable medical device using the non-rechargeable battery while the second energy level is above a predetermined threshold; and
  powering the implantable medical device using the rechargeable battery while the second energy level is not above the predetermined threshold.

30. The method of claim 28, comprising:
  powering the implantable medical device using the rechargeable battery while the first energy level is above a predetermined threshold; and
  powering the implantable medical device using the non-rechargeable battery while the first energy level is not above the predetermined threshold.

31. The method of claim 28, wherein detecting at least one of the first energy level and the second energy level comprises detecting a parameter indicative of a state of charge of at least one of the rechargeable battery and the non-rechargeable battery.

32. The method of claim 31, further comprising producing one or more warning signals using the parameter indicative of the state of charge.

33. A system, comprising:
an implantable sensor module including:
- a pressure sensor to sense a signal indicative of a blood pressure; and
- a power source adapted to provide power to the pressure sensor, the power source including:
  - a rechargeable battery;
  - a battery status monitor coupled to the rechargeable battery, the battery status monitor adapted to detect an energy level of the rechargeable battery;
  - a recharging controller coupled to the battery status monitor, the recharging controller adapted to control a process of recharging the rechargeable battery using the energy level; and
  - a recharging circuit coupled to the recharging controller and the rechargeable battery, the recharging circuit including:
    - an ultrasonic power receiver to receive an ultrasonic signal carrying an ultrasonic energy and having a frequency in a range between 38 kHz and 42 kHz; and
    - a piezoelectric transducer to convert the ultrasonic energy to an electrical energy for recharging the rechargeable battery.

34. The system of claim 33, wherein the implantable sensor module comprises an implant telemetry circuit adapted to transmit data representative of the sensed signal to another implantable device.

35. The system of claim 34, further comprising an external system communicatively coupled to the implantable sensor module, and wherein the implant telemetry circuit is further adapted to transmit the data representative of the sensed signal to the external system.

36. The system of claim 33, further comprising:
an external system to transmit the ultrasonic signal; and
an integrated ultrasonic data transmission and power transmission link coupling between the external system and the implantable sensor module,
and wherein the ultrasonic power receiver is adapted to receive the ultrasonic signal via the integrated ultrasonic data transmission and power transmission link, the ultrasonic signal modulated for data transmission.

37. The system of claim 33, wherein the battery status monitor comprises means for detecting a parameter indicative of a state of charge of the rechargeable battery.

38. The system of claim 37, wherein the battery status monitor comprises a warning signal generator adapted to produce one or more warning signals using the parameter indicative of the state of charge.

39. A method for operating a medical device system, the method comprising:
sensing a signal indicative of a blood pressure using a first implantable medical device;
powering a circuit of the first implantable medical device using a rechargeable battery;
detecting an energy level of the rechargeable battery;
receiving an ultrasonic signal carrying an ultrasonic energy from an external system, the ultrasound signal having a frequency in a range between 38 kHz and 42 kHz;
converting the ultrasonic energy to an electrical energy;
recharging the rechargeable battery using the electrical energy; and
controlling the recharging the rechargeable battery using the energy level.

40. The method of claim 39, further comprising transmitting data representative of the sensed signal to a second implantable medical device.

41. The method of claim 40, further comprising transmitting the data representative of the sensed signal to an external system.

42. The method of claim 39, further comprising transmitting data from the external system to the first implantable medical device by modulating the ultrasonic signal.

43. The method of claim 39, wherein detecting the energy level comprises detecting a parameter indicative of a state of charge of the rechargeable battery.

44. The method of claim 43, further comprising producing one or more warning signals using the parameter indicative of the state of charge.

* * * * *